United States Patent
Tan et al.

(10) Patent No.: US 10,384,040 B1
(45) Date of Patent: *Aug. 20, 2019

(54) SUMP PORT DRAIN ADAPTER (71) Applicant: Summa Health, Akron, OH (US)

(72) Inventors: Eugene Mark Tan, Akron, OH (US); James Rorar, Akron, OH (US)

(73) Assignee: Summa Health, Akron, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/962,786

(22) Filed: Dec. 8, 2015

Related U.S. Application Data (60) Provisional application No. 62/088,939, filed on Dec. 8, 2014.

(51) Int. Cl.
*A61M 27/00* (2006.01)
*A61J 15/00* (2006.01)
*A61M 39/12* (2006.01)

(52) U.S. Cl.
CPC .......... *A61M 27/00* (2013.01); *A61J 15/0003* (2013.01); *A61J 15/0053* (2013.01); *A61M 39/12* (2013.01)

(58) Field of Classification Search
CPC .... A61M 27/00; A61M 39/12; A61M 1/0001; A61M 1/0019; A61M 1/0021; A61M 1/0013; A61M 1/0049; A61J 15/0003; A61J 15/0053; A61J 15/0073; A61J 15/0026

See application file for complete search history.

(56) References Cited

U.S. PATENT DOCUMENTS

| | | | | |
|---|---|---|---|---|
| 5,087,250 A | * | 2/1992 | Lichte | A61M 1/3627 604/319 |
| 5,417,664 A | * | 5/1995 | Felix | A61M 1/008 604/129 |
| 5,722,964 A | * | 3/1998 | Herweck | A61M 1/0013 604/317 |
| 6,322,834 B1 | * | 11/2001 | Leone | A23F 3/385 426/422 |
| 8,100,874 B1 | * | 1/2012 | Jordan | A61M 1/0001 604/19 |
| 9,668,909 B1 | * | 6/2017 | Lormand-Koch | A61F 5/4407 |
| 2014/0121618 A1 | * | 5/2014 | Cesa | A61J 1/10 604/327 |

* cited by examiner

*Primary Examiner* — Adam Marcetich
*Assistant Examiner* — Jessica R Arble
(74) *Attorney, Agent, or Firm* — FisherBroyles, LLP (57) ABSTRACT

A sump port drain adapter apparatus is disclosed which provides a small, lightweight vessel to capture and collect gastric reflux or stomach contents exiting the smaller lumen, or sump line, of a double lumen nasogastric tube while providing airflow to the sump line to prevent the nasogastric tube from adhering to the stomach lining. The apparatus disclosed prevents clogging in the sump line, unnecessary patient gown and bedding changes, patient skin breakdown and decreases exposure to potentially infectious material for both the patient and healthcare workers.

10 Claims, 5 Drawing Sheets

SUMP PORT DRAIN ADAPTER

This application claims the benefit of U.S. Provisional Patent Application Ser. No. 62/088,939 filed Dec. 8, 2014.

A sump port drain adapter apparatus, system and method are disclosed. In one embodiment, when used in conjunction with a double lumen nasogastric tube, the sump port drain adapter apparatus allows air into the stomach to prevent the nasogastric tube from adhering to the stomach lining while preventing a patient from aspirating stomach contents. The sump port drain adapter apparatus may be fastened to a patient's dressing gown or bedside to allow for the collection of gastric reflux or stomach content from the smaller lumen, or sump line, into the apparatus. The apparatus may prevent clogging of the sump line, prevent unnecessary patient gown and bedding changes, prevent patient skin breakdown and may decrease exposure to potentially infectious material for both the patient and healthcare workers.

BRIEF DESCRIPTION OF THE DRAWINGS

The accompanying drawings, which are incorporated in and constitute a part of the specification, illustrate various example apparatuses, systems, methods, and so on, that illustrate various embodiments of aspects of the invention. It will be appreciated that the illustrated element boundaries (e.g., prisms, boxes, groups of boxes, or other shapes) in the figures represent one example of the boundaries. One of ordinary skill in the art will appreciate that one element may be designed as multiple elements or that multiple elements may be designed as one element. An element shown as an internal component of another element may be implemented as an external component and vice versa. Furthermore, elements may not be drawn to scale and in some instances, cross-hatching is not shown to improve clarity.

DETAILED DESCRIPTION

Figure 1:
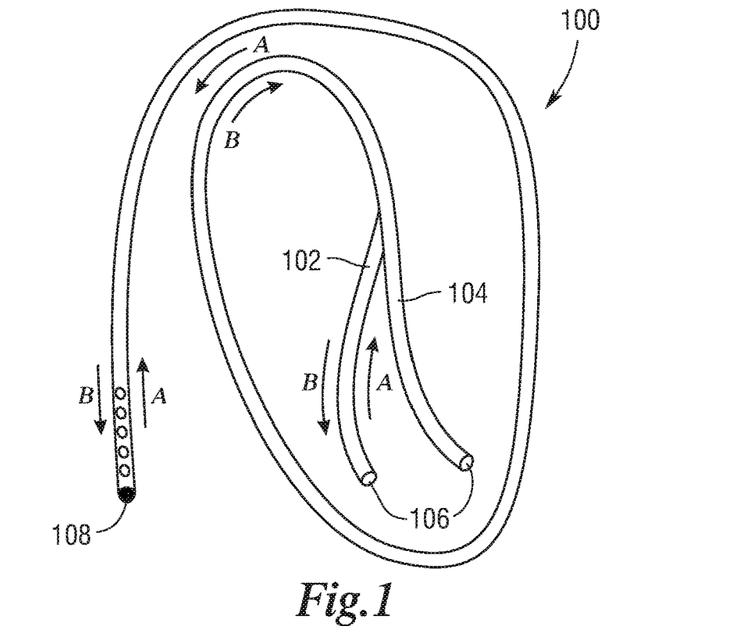
FIG. 1 is an exemplary view of a double lumen nasogastric tube.

With reference to FIG. 1, a nasogastric tube 100 is shown with two lumens. The second or smaller lumen 102, a sump port or sump line, extends at some distance from the proximal end 106 of the larger lumen 104. In use, the distal end 108 of the larger lumen 104 may be inserted in the stomach of a patient (not shown), while the proximal end 106 of the larger lumen 104 and the sump line 102 extend outside of a patient. In use, the sump line 102 may allow air, whose flow is indicated by arrow A, into the stomach to reduce the chance of adherence of the distal end 108 of the larger lumen 104 to a patient's stomach mucosa or lining when the distal end 108 of the larger lumen 104 is inserted into the stomach or placed in the stomach for activities including suctioning, draining, and/or feeding.

In use, leakage of gastric reflux or stomach contents from the distal end 108 of the larger lumen of the nasogastric tube 104 into the sump line 102, which flow is indicated by arrow B, may be prevented by a valve (not shown). The valve may allow the passage of air into the sump line 102, as indicated by arrow A, when the atmospheric pressure exceeds the pressure in the patient's stomach. Conversely, the valve may prevent the flow of liquids through the sump line 102 when the pressure in the patient's stomach exceeds the atmospheric pressure.

Conventional anti-reflux valves (not shown) are typically comprised of paper one-way valves to allow the passage of air into a patient's stomach and to prevent gastric reflux or leakage of stomach contents up the sump line 102 of a double lumen nasogastric tube 100. The paper anti-reflux valve often gets saturated from gastric fluids traveling from the distal end 108 of a double lumen nasogastric tube 100 into the sump line 102, which flow is indicated by arrow B. Once saturated, the paper anti-reflux valve fails to function and prevents air from entering the sump line 102 to travel through the distal end 108 of the nasogastric tube 100 to the stomach, which flow is indicated by arrow A. If the flow of air into the stomach is prevented, the distal end 108 of the nasogastric tube 100 may adhere to the stomach mucosa causing injury to the patient. A patient also may aspirate stomach content as a result of the clogging of the anti-reflux valve. To prevent the failure of conventional anti-reflux valves and to insure air flow through the sump line 102, some doctors order the removal of the anti-reflux valve from the double lumen nasogastric tube 100. Although the removal of the anti-reflux valve from the double lumen nasogastric tube 100 allows air to flow through the sump line 102, the removal also allows gastric fluid to exit the stomach through the sump line 102, which flow is indicated by arrow B. These gastric fluids may drain onto the surrounding area and saturate patient's clothing or bedding, which may result in discomfort and increased risk of skin injury to the patient due to the acidic nature of stomach contents. The leakage of gastric fluids may also increase a patient's and healthcare workers' risk of exposure to infectious material and may result in increased frequency of changes to the patient's clothing and bedding.

One embodiment of an apparatus, system and method as used herein includes but is not limited to a sump port drain adapter apparatus including a sump port connector capable of securely attaching to the sump line of a double lumen nasogastric tube to collect and contain the leakage of gastric reflux or stomach contents from a patient's stomach while allowing air to enter the patient's stomach. By eliminating the need for anti-reflux valves, the apparatus prevents injury to a patient from an undetected malfunction of an anti-reflux valve, prevents clogging in the sump line and prevents the aspiration of stomach contents by the patient. The preferably small size of the apparatus may facilitate its use without interfering with patient positioning or comfort. The apparatus also may prevent unnecessary patient gown and bedding changes, patient skin breakdown and may decrease exposure to potentially infectious material to both the patient and healthcare workers. As more completely discussed below, the sump port drain adapter apparatus may include but is not limited to a sump port connector, an air vent, an air vent cap, a funnel with a hole, a fluid catcher, an overflow chamber, a drain hole, a tube plug, a tie with cap to secure the drain hole and a fastener to secure the apparatus which may result in increased stability of the apparatus and may prevent inadvertent leakage from the apparatus.

Figure 2:
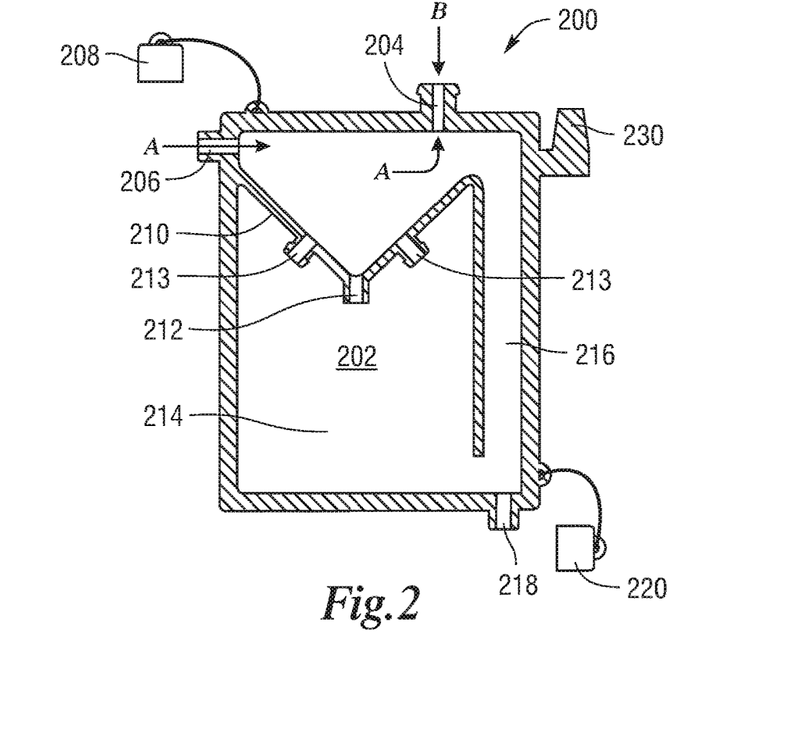
FIG. 2 is a front cross-sectional view of an exemplary sump port drain adapter apparatus to illustrate internal components.

With reference to FIG. 2, an exemplary apparatus 200 for a sump port drain adapter is shown. One embodiment of a sump port drain adapter apparatus 200, includes but is not limited to a vessel, housing or container 202 in the shape of a rectangular prism which may be approximately 3.5 inches in height, 2.5 inches in width and 0.75 inches in depth. The vessel 202 is not limited to these dimensions and may be comprised of different dimensions or shapes. The apparatus 200 also may be comprised of a number of different materials which have the ability to capture or collect acid reflux, gastric fluids or similar materials without penetrating or permeating the vessel 202 or other components of the apparatus. For example, the vessel 202 may be comprised of a certain type of plastic that has the ability to prevent penetration or permeation by materials such as acid reflux or gastric fluids while maintaining its structure and resisting breakage. The vessel 202 also may be comprised of lightweight materials to preferably decrease its weight and increase patient comfort. The vessel 202 also may be comprised of a transparent material to allow visual determination of the amount of acid reflux, gastric fluids or similar materials collected.

The apparatus also may include an orifice designated as a sump port connector 204 located at and extending from the top face of the vessel 202 for insertion into the proximal end 106 of the sump line 102 of a double lumen nasogastric tube 100. Alternatively, the sump port connector 204 may extend from the top of the apparatus 200 into the vessel 202 allowing for the insertion of the proximal end 106 of the sump line 102 into the vessel 202 extending through to the sump port connector 204 (indicated by dashed lines). The sump port connector 204 may be located off-center of the top face of the vessel 202 as shown, or otherwise conveniently positioned. In use, a path of fluid communication from the stomach through the sump line 102, is indicated by arrow B. While fluid communication may refer to liquid fluids as here gastric fluids are presumed, the term fluid communication may instead or in addition refer to a path for gaseous communication. Accordingly, the path of fluid communication permits gastric reflux or stomach contents to flow from the sump line 102 (not shown) of the nasogastric tube into the apparatus 200 through sump port connector 204, which flow is indicated by arrow B. The apparatus may include a sump port connector 204 that is capable of securely attaching to various diameters of double lumen nasogastric tubes including but not limited to adult or pediatric naso gastric tubes.

The apparatus 200 also may include an air vent 206 to allow a path of fluid communication permitting air to enter the apparatus, flow through the upper portion of the vessel 202 and exit through the sump port connector 204, in the direction of arrow A. The air vent 206 allows airflow into the sump line 102 for reasons including but not limited to preventing the distal end 108 of the nasogastric tube 100 from adhering to the lining of a patient's stomach and assisting in the movement of material through the nasogastric tube. The air vent 206 may be located at the top peripheral edge farthest from where the sump port connector 204 is located. In FIG. 2, the diameter of the air vent 206 is illustrated as approximately 0.25 inches, but its diameter may vary in size depending on various factors including, but not limited to, tube purpose and patient size. The apparatus 200 may further include an air vent cap 208 for the air vent 206 which may allow the flow of air through the apparatus 200 to be restricted or interrupted. In FIG. 2, the air vent cap 208 is illustrated as remaining attached to the vessel 202 when disengaged, but the air vent cap 208 may be part of the air vent 206 or may be separate and independent from the vessel 202 when removed from the air vent 206.

The apparatus 200 also may include a shaped fluid guide, such as a funnel 210 located in the interior of the vessel 202 which funnel 210 may extend symmetrically or asymmetrically in a downward direction from the lower edge area of the air vent 206. For example, an upper side of the funnel 210 may form a portion of an upper reservoir in contact with the base of the air vent 206 so that the funnel does not obstruct the air vent 206 and may extend 1 inch to 1.5 inches in a downward direction. In FIG. 2, the top plane of the funnel 210 is illustrated as approximately 0.25 inches from the top of the vessel 202 and is in communication with the top of an overflow chamber 216 located at the opposite side of the vessel 202 as the air vent 206. The funnel 210 is not limited to these dimensions or the orientation illustrated and may be comprised of different sizes, shapes or orientation in the vessel 202. At least one orifice, or funnel hole 212, may be located at the approximate mid-point of the vessel and may direct the flow of acid reflux, gastric fluids or similar materials entering the vessel from the sump port connector 204 to a lower portion of the vessel 202 for collection. The funnel 210 may be comprised of the same or different materials as the vessel 202. In one embodiment, a single funnel hole 212 may be disposed as illustrated, namely toward a bottom or lower side of funnel 210. Alternately or additionally, secondary funnel holes 213 may be disposed part-way up the funnel wall to provide alternate or additional paths for fluid communication between the upper reservoir of the vessel 202 and a fluid catching basin or reservoir 214. The diameter of the funnel hole 212 and/or secondary funnel holes 213 may be approximately 0.125 inches, but the diameter may vary in size depending on various factors.

The fluid retention basin 214 in a lower portion of the vessel 202 collects the acid reflux, gastric fluids or similar materials flowing from the sump port connector 204 through the funnel hole 212 and/or the secondary funnel holes 213. The atmospheric air pressure from the air vent 206 along with gravity may assist in moving the stomach contents into the fluid basin 214. The fluid basin 214 may include the lower, interior base of the vessel 202 and extend upward to include the area surrounding the base of the shaped funnel 210. The funnel 210 may assist in preventing flow of fluid from the fluid basin 214 to the upper portion of the vessel 202 and possibly back into a connected nasogastric tube 100 as a result of movement of the vessel 202 or of the patient.

The apparatus 200 may further include an overflow chamber 216 illustrated as being located at the opposite side of the vessel 202 relative to the air vent 206, which overflow chamber 216 is in communication with the area above the funnel 210 and may collect acid reflux, gastric fluids or similar materials which may be unable to be directed to fluid basin 214 or through funnel hole 212, 213. For example, the overflow chamber 216 may be approximately 0.25 inches in diameter. The overflow chamber 216 may prevent obstruction of the air flow from the air vent 206 to the sump line 102. The overflow chamber 216 also may be in fluid communication with the fluid catcher 214 near the base of the overflow chamber 216. The overflow chamber 216 may extend beyond the bottom face of the vessel 202 to facilitate drainage of acid reflux, gastric fluids or similar materials from the apparatus 200. The overflow chamber 216 may be comprised of different dimensions or shapes than illustrated in FIG. 2. In an embodiment, a visible surface of the vessel 202 may include graduation markings indicating the volume of fluid contained in the fluid catcher.

The apparatus 200 may further include an orifice, or drain hole 218, at the base of the vessel 202 which may allow acid reflux, gastric fluids or similar materials to be drained or removed from the apparatus 200. The diameter of the drain hole 218 is illustrated as approximately 0.25 inches, but its diameter may vary in size depending on various factors. The drain hole 218 also may include a valve or similar device to control or interrupt the flow of acid reflux, gastric fluids or similar materials from the apparatus 200. The apparatus 200 may further include a tie with cap 220 for the drain hole 218 which may allow the flow of acid reflux, gastric fluids or similar materials from the apparatus 200 to be restricted or interrupted. The tie with cap 220 will normally be closed or capped. In FIG. 2, the tie with cap 220 is illustrated as remaining attached to the vessel 202, but the tie with cap 220 may be part of the drain hole 218 or may be separate and independent from the vessel 202 when removed from the drain hole 218. Alternatively, the base of the overflow chamber 216 at the drain hole 218 may include any variation of valves, drains and the like that may control the flow of acid reflux, gastric fluids or similar materials from the apparatus 200. For example, the release of materials from the drain hole 218 may be accomplished by removing a clip and flexing and extending a drain plug out of the drain hole 218 to allow drainage and retracting the drain plug into the drain hole 218 and replacing the clip to restrict or interrupt drainage. In an embodiment, the apparatus 200 may further include an NG tube plug 230 that may act as a tapered attachment point for end 106 of the larger lumen 104 (FIG. 1). The location of the NG tube plug may be on a side of the apparatus as shown or otherwise conveniently located.

Figure 3:
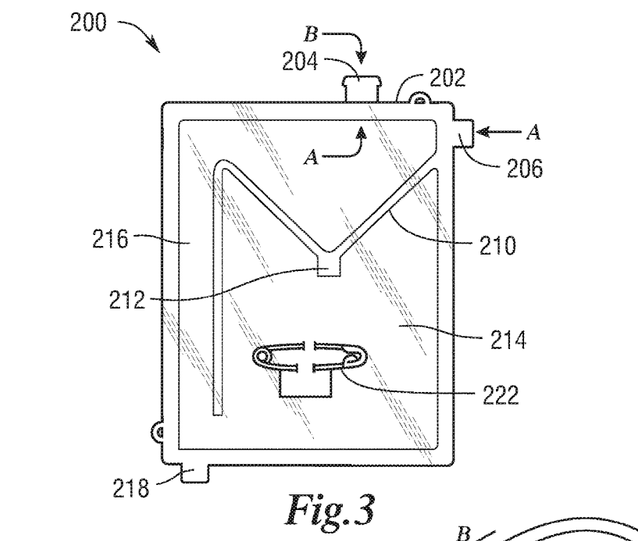
FIG. 3 is a back view of an exemplary transparent sump port drain adapter apparatus to illustrate internal components.

With reference to FIG. 3, a back view of an exemplary apparatus 200 for a sump port drain adapter with a transparent housing to permit monitoring of fluid levels within the vessel 202. Vessel 202 may be connected for use with a double lumen nasogastric tube 100, although only illustrating a single funnel hole 212. In addition to components that may be included as part of the apparatus 200 as described in reference to FIG. 2, the apparatus 200 also may include a fastener 222 which may be secured to the back of the vessel 202 and to another object or device (not shown). The use of a fastener 222 may result in increased stability of the apparatus 200 and may prevent acid reflux, gastric fluids or similar materials from exiting the apparatus 200 inadvertently. In FIG. 3, the fastener 222 is illustrated as a safety pin, but the fastener 222 may be comprised of a number of different materials which have the ability to secure the apparatus 200 to another object or device. For example, the apparatus 200 may be secured by the fastener 222 to a patient's gown (not shown) or a hospital bed (not shown).

Figure 4:
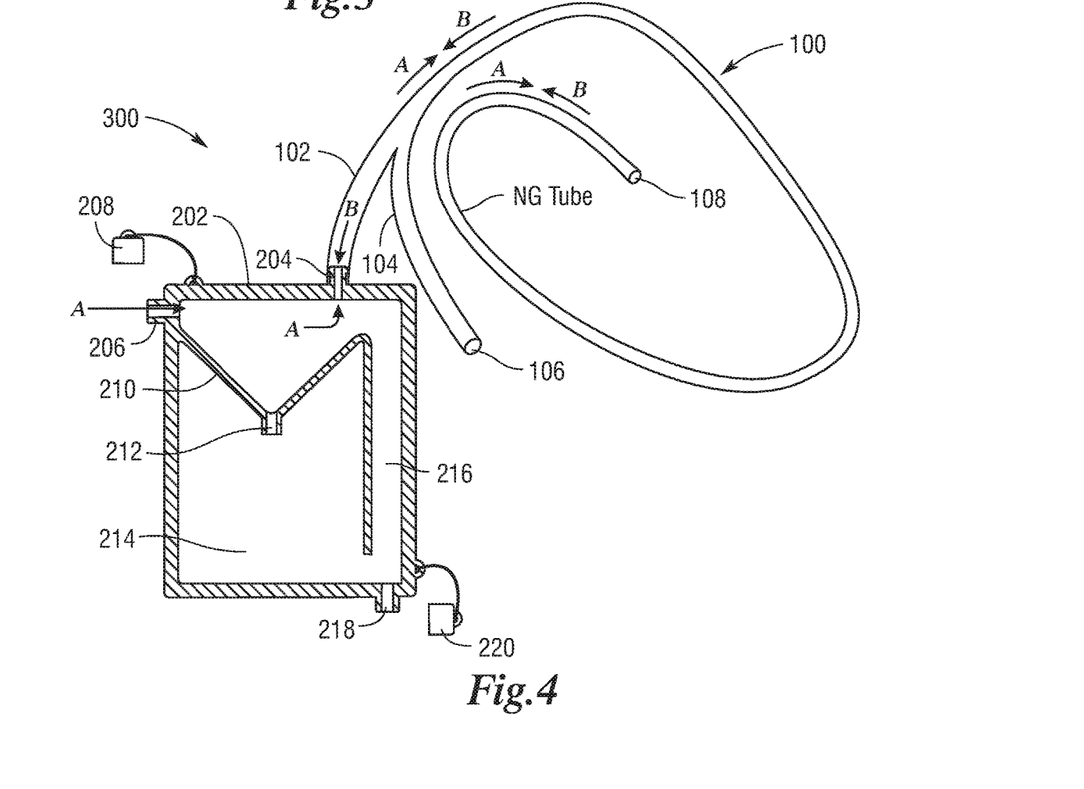
FIG. 4 is a front cross-sectional view of a sump port drain adapter apparatus connected to the sump line of a double lumen nasogastric tube.

With reference to FIG. 4, a front view of an exemplary apparatus 300 for a sump port drain adapter includes a sump line 102 of a double lumen nasogastric tube 100 connected or attached to a vessel 202. In use, gastric reflux or stomach content may flow from a patient's stomach through the sump line 102 of the nasogastric tube into the vessel 202 through sump port connector 204, which flow is indicated by arrow B. In use, the vessel 202 also may include an air vent 206 to allow air to enter the apparatus, flow through the upper portion of the vessel 202 and exit through the sump port connector 204 into the sump line 102 of the nasogastric tube 100 into a patient's stomach, in the direction of arrow A.

Figures 5, 6:
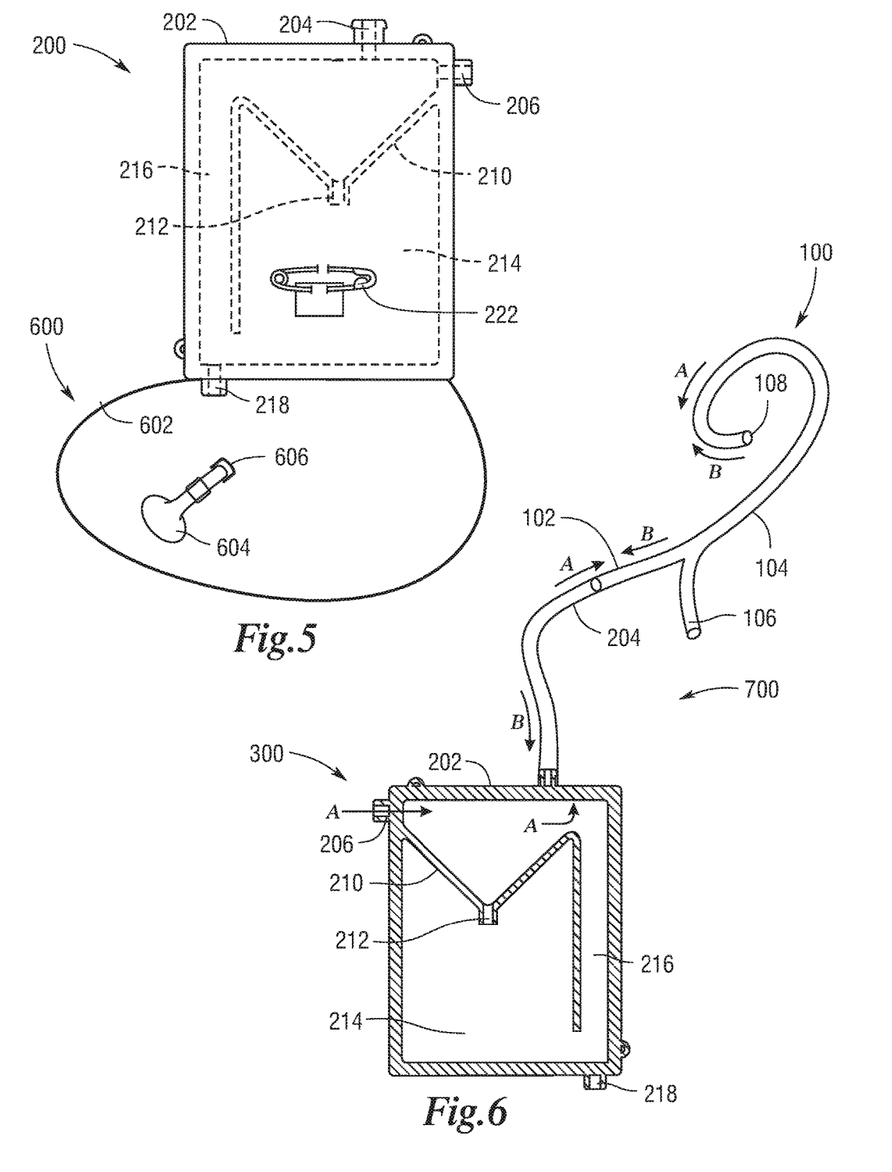
FIG. 5 is a back view of an embodiment of an exemplary sump port drain adapter apparatus including a reservoir which increases capacity to collect and drain acid reflux, gastric fluids or similar materials.
FIG. 6 is a front view of another embodiment of an exemplary sump port drain adapter apparatus (in cross section to illustrate internal components) connected to the sump line of a double lumen nasogastric tube showing an alternative design of the sump port connector.

With reference to FIG. 5, another embodiment of an exemplary system 200 includes a sump port drain adapter 200 attached to an additional reservoir 600. In this embodiment, the system 200 may include a flexible receptacle 602 connected to the drain hole 218 which may accept acid reflux, gastric fluids or similar materials exiting the vessel 202. The flexible receptacle 602 may allow an increased volume of acid reflux, gastric fluids or similar materials to be collected or captured which may result in decreasing the frequency of the drainage of or the replacement of the vessel 202. The flexible receptacle 602 may be in the form of a bag which increases in size as the materials fill the flexible receptacle 602 or may be comprised of various dimensions or shapes. The flexible receptacle 602 also may be comprised of a number of different materials which have the ability to capture or collect acid reflux, gastric fluids or similar materials without penetrating or permeating the flexible receptacle 602 or any components of the flexible receptacle 602. For example, the flexible receptacle 602 may be comprised of a certain type of plastic that has the ability to prevent penetration or permeation by materials such as acid reflux or gastric fluids while resisting breakage. The flexible receptacle 602 also may be comprised of lightweight materials to preferably decrease weight and increase patient comfort. The flexible receptacle 602 may further be comprised of a transparent material to allow visual determination of the amount of acid reflux, gastric fluids or similar materials collected. The flexible receptacle 602 also may include a drain plug 604 and clip 606 that may control the release of acid reflux, gastric fluids or similar materials from the flexible receptacle 602. For example, the release of materials from the flexible receptacle 602 may be accomplished by removing the clip 606 and flexing and extending the drain plug 604 out of the flexible receptacle 602 to allow drainage and retracting the drain plug 604 into the flexible receptacle 602 and replacing the clip 606 to restrict or interrupt drainage. The connection between the flexible receptacle 602 and the vessel 202 also may facilitate ease of disposal and replacement of the flexible receptacle 602 as required.

With reference to FIG. 6, in another embodiment 700, a sump port drain adapter 200 may include a sump port connector 204 that extends beyond the vessel 202 to connect or attach to the proximal end 106 of the sump line 102 of a double lumen nasogastric tube 100 so that the vessel 202 may be generally accessible to healthcare workers without being in direct contact with the patient. For example, the vessel 202 may be placed at a distance from the patient such as on a table, pole or floor or attached to the patient's bed. Alternatively, the connection or attachment between the sump port connector 204 and the proximal end 106 of the sump line 102 of a double lumen nasogastric tube 100 may be comprised of a separate or independent lumen or other device (not shown).

Figures 7, 8:
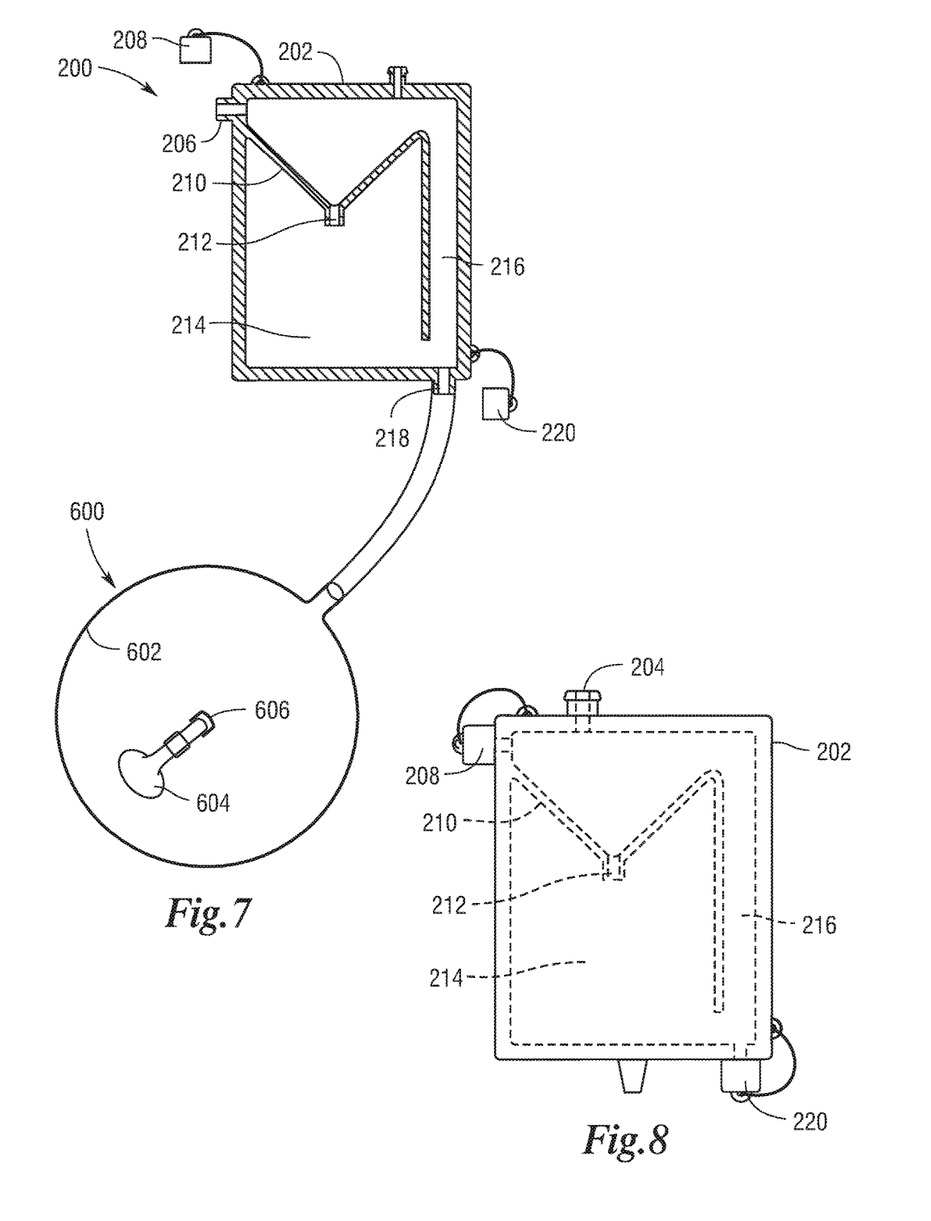
FIG. 7 is a front view of another embodiment of an exemplary sump port drain adapter apparatus (in cross section to illustrate internal components) showing an alternative design of a connector or attachment to the drain hole of the sump port drain adapter apparatus to a component which increases capacity to collect and drain acid reflux, gastric fluids or similar materials.
FIGS. 8 and 9 are views of another embodiment of an exemplary sump port drain adapter apparatus.

With reference to FIG. 7, in another embodiment 800, a sump port drain adapter 200 may include a connector or attachment 801 to the drain hole 218 that extends beyond the vessel 202 to secure to the flexible receptacle 602 so that the flexible receptacle 602 may be generally accessible without being in direct contact with the patient. For example, the flexible receptacle 602 may be attached to the patient's bed, placed on a table or floor or hung on a hanger or pole. The connector or attachment 801 between the drain hole 218 and the flexible receptacle 602 may be part of the drain hole 218 or of the flexible receptacle 602. Alternatively, the connection or attachment 801 between the drain hole 218 and the flexible receptacle 602 may be comprised of a separate or independent lumen or other device (not shown).

Figure 9:
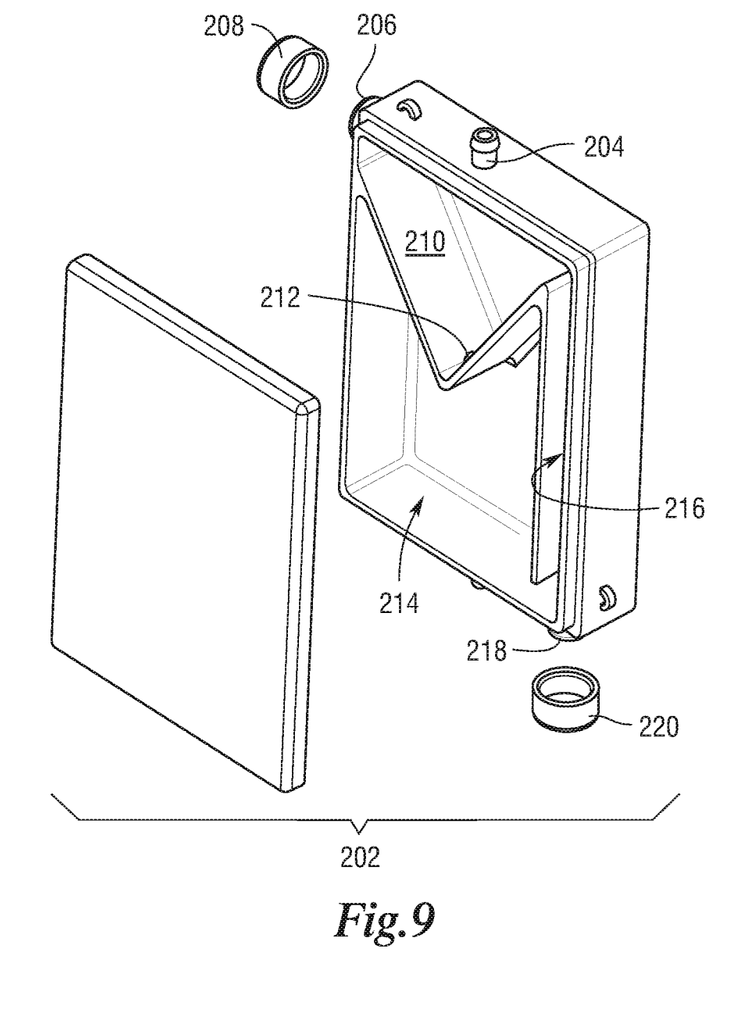

With reference to FIGS. 8 and 9, another embodiment of a vessel 202 is illustrated.

While the apparatuses, systems and methods and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the apparatuses, systems and methods, and so on provided herein. Additional advantages and modifications will readily appear to those skilled in the art. Therefore, the invention, in its broader aspects, is not limited to the specific details, the representative apparatus, and illustrative examples shown and described. Accordingly, departures may be made from such details without departing from the spirit of scope of the applicants' general inventive concept. The sump port drain adapter apparatus is not limited to use with a double lumen nasogastric tube and may be used with other devices or systems both within and outside of the medical field. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalent.

As used herein, "connection" or "connected" means both directly, that is, without other intervening elements or components, and indirectly, that is, with another component or components arranged between the items identified or described as being connected. To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the claims (e.g., A or B) it is intended to mean "A or B or both". When the applicants intend to indicate "only A or B but not both" then the term "only A or B but not both" will be employed. Similarly, when the applicants intend to indicate "one and only one" of A, B, or C, the applicants will employ the phrase "one and only one". Thus, use of the term "or" herein is the inclusive, and not the exclusive use. See, Bryan A. Garner, A Dictionary of Modern Legal Usage 624 (2d. Ed. 1995).

What is claimed is:

1. A sump port drain adapter comprising
   A vessel housing;
   A sump port connector intersecting the vessel housing providing a first path for fluid communication to and from an interior of the vessel housing, where the sump port connector is connectable to a sump line of a double lumen nasogastric tube;
   A vent intersecting the vessel housing at a location spaced from the sump port connector, the vent providing a second path for fluid communication to and from the interior of the vessel housing;
   A vent cap connectable to the vent, selectively interrupting the second path of fluid communication;
   A shaped fluid guide disposed within the interior of the vessel housing and arranged in a spaced relation from the vent and the sump port connector to permit liquid or solid materials entering the vessel housing through the sump port connector to flow through an orifice in the shaped fluid guide, where the shaped fluid guide and the orifice define a base of an upper reservoir in direct fluid communication with the sump port connector and the vent;
   A lower chamber within the vessel opposite the upper reservoir and defined on a top side by the shaped fluid guide and the orifice, the lower chamber collecting the liquid or solid materials from the orifice in the shaped fluid guide, and where a path for fluid communication between the vent and the lower chamber is provided through the orifice;
   An overflow chamber connected to the lower chamber on one side such that the overflow chamber provides a second path of fluid communication excluding the orifice between the lower chamber, the overflow chamber and the upper reservoir;
   A drain access disposed on a lower side of the lower chamber providing a path for drain fluid communication from the lower chamber;
   A drain hole cap connectable to the drain access, the drain hole cap permitting user control of materials exiting the vessel; and
   A fastener connected on an external surface of the vessel housing, the fastener connectable to clothing or other objects.

2. The sump port drain adapter as set forth in claim 1, further comprising a receptacle connected to the drain access and disposed external to vessel housing permitting removal of materials from the vessel housing.

3. The sump port drain adapter as set forth in claim 2, where the receptacle further comprises a drain permitting removal of materials from the receptacle.

4. The sump port drain adapter as set forth in claim 1, where the sump port connector extends away from the vessel housing a distance sufficient to prevent direct contact between the vessel housing and a terminal end of the double lumen nasogastric tube.

5. The sump port drain adapter as set forth in claim 2, further comprising an elongated attachment connected at a first proximal side to the drain access and connected at a second distal side to the receptacle at a distance sufficient to dispose the receptacle remotely from the vessel housing.

6. A system comprising:
   A double lumen nasogastric tube;
   A sump port drain adapter connected to the double lumen nasogastric tube, the sump port drain adapter including:
      A vessel housing;
      A sump port connector intersecting the vessel housing providing a first path for fluid communication to and from an interior of the vessel housing, where the sump port connector is connectable to a sump line of the double lumen nasogastric tube;
      A vent intersecting the vessel housing at a location spaced from the sump port connector, the vent providing a second path for fluid communication to and from the interior of the vessel housing;
      A shaped fluid guide disposed within the interior of the vessel housing disposed to define an upper reservoir and a lower chamber, where the shaped fluid guide defines a narrowing path of fluid communication from the vent and the sump port connector to direct liquid or solid materials entering the interior of the vessel housing through the sump port connector to flow through an orifice in the shaped fluid guide for retention in the lower chamber;

An overflow chamber adjacent to the upper reservoir and the lower chamber and providing an alternate path of fluid communication between the upper reservoir and the lower chamber, where the alternate path bypasses the orifice; and A drain access disposed on a lower side of the vessel housing providing a path for drain fluid communication from the chamber.

7. The sump port drain adapter as set forth in claim 6, where the shaped fluid guide comprises a plurality of funnel holes permitting liquid fluid communication from the upper reservoir to the lower chamber and impeding liquid fluid communication from the lower chamber to the upper reservoir.

8. The sump port drain adapter as set forth in claim 6, further comprising a receptacle connected to the drain access and disposed external to vessel housing permitting removal of materials from the vessel housing.

9. The sump port drain adapter as set forth in claim 6, where the sump port connector extends away from the vessel housing a distance sufficient to prevent direct contact between the vessel housing and a terminal end of the double lumen nasogastric tube.

10. The sump port drain adapter as set forth in claim 8, further comprising an elongated attachment connected at a first proximal side to the drain access and connected at a second distal side to the receptacle at a distance sufficient to dispose the receptacle remotely from the vessel housing.

* * * * *